(12) United States Patent
Veldman et al.

(10) Patent No.: US 7,753,940 B2
(45) Date of Patent: Jul. 13, 2010

(54) LATERAL CONNECTOR ASSEMBLY

(75) Inventors: Michael S. Veldman, Memphis, TN (US); Doug Baker, Collierville, TN (US); Marco D. Capote, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 654 days.

(21) Appl. No.: 11/398,371

(22) Filed: Apr. 5, 2006

(65) Prior Publication Data
US 2007/0238335 A1 Oct. 11, 2007

(51) Int. Cl.
*A61B 17/70* (2006.01)
(52) U.S. Cl. ...................................... 606/278
(58) Field of Classification Search ................. 606/278, 606/297, 300, 324, 328, 60, 66, 246–247, 606/250–253, 277
See application file for complete search history.

(56) References Cited

U.S. PATENT DOCUMENTS

| | | | |
|---|---|---|---|
| 5,261,909 A | | 11/1993 | Sutterlin et al. |
| 5,282,801 A | | 2/1994 | Sherman |
| 5,643,263 A | * | 7/1997 | Simonson ................. 606/278 |
| 5,885,285 A | | 3/1999 | Simonson |
| 5,976,135 A | * | 11/1999 | Sherman et al. ........... 606/278 |
| 6,183,473 B1 | * | 2/2001 | Ashman .................... 606/278 |
| 6,210,413 B1 | * | 4/2001 | Justis et al. ............... 606/254 |
| 6,471,703 B1 | | 10/2002 | Ashman |
| 6,520,962 B1 | | 2/2003 | Taylor et al. |
| 6,572,618 B1 | * | 6/2003 | Morrison ................... 606/278 |
| 6,579,292 B2 | | 6/2003 | Taylor |
| 7,261,715 B2 | * | 8/2007 | Rezach et al. ............... 606/60 |
| 7,575,587 B2 | * | 8/2009 | Rezach et al. .............. 606/278 |
| 7,651,516 B2 | * | 1/2010 | Petit et al. .................. 606/279 |
| 2003/0105460 A1 | * | 6/2003 | Crandall et al. ............. 606/61 |
| 2003/0139745 A1 | * | 7/2003 | Ashman ..................... 606/61 |
| 2003/0176862 A1 | * | 9/2003 | Taylor et al. ................ 606/61 |
| 2003/0191473 A1 | * | 10/2003 | Taylor ........................ 606/61 |
| 2005/0113830 A1 | * | 5/2005 | Rezach et al. ............... 606/60 |
| 2005/0137594 A1 | * | 6/2005 | Doubler et al. ............. 606/61 |

(Continued)

FOREIGN PATENT DOCUMENTS

EP 0734688 A1 10/1996

OTHER PUBLICATIONS

European Patent Office, International Searching Authority, Notification of Transmittal of the International Search Report and the Written Opinion of the International Searching Authority, or the Declaration, International Application No. PCT/US2007/065420, International Search report mailing date Mar. 4, 2008.

*Primary Examiner*—Thomas C Barrett
*Assistant Examiner*—Larry E Waggle, Jr.

(57) ABSTRACT

A lateral connector assembly for connecting a bone engaging fastener to an elongated member, such as a spinal rod includes a lateral connector having an opening for receiving a portion of the bone engaging fastener therethrough. The lateral connector includes a plate portion and an integral yoke portion, which yoke portion is attached to the elongated member by way of a clamp. The lateral connector assembly can include variable angle means between the clamp and the yoke portion of the lateral connector that permits rotation of the lateral connector about an axis projecting outward from the spinal rod. The clamp includes a tapering channel to capture the elongated member and lock the connector assembly.

20 Claims, 3 Drawing Sheets

U.S. PATENT DOCUMENTS

2006/0195096 A1* 8/2006 Lee et al. .................. 606/61
2006/0217718 A1* 9/2006 Chervitz et al. ............ 606/61
2006/0247628 A1* 11/2006 Rawlins et al. ............ 606/61

* cited by examiner

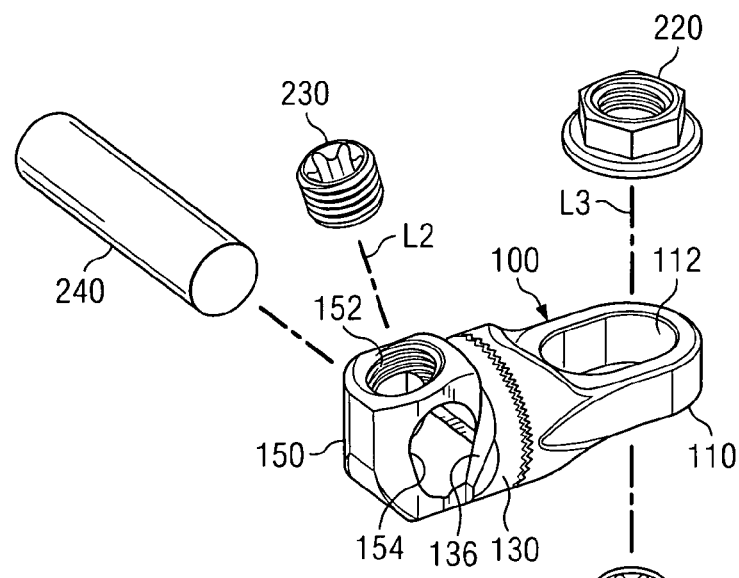
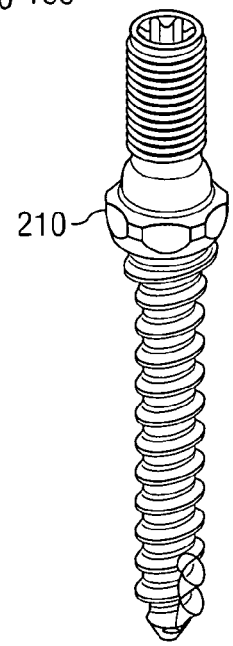
Fig. 2
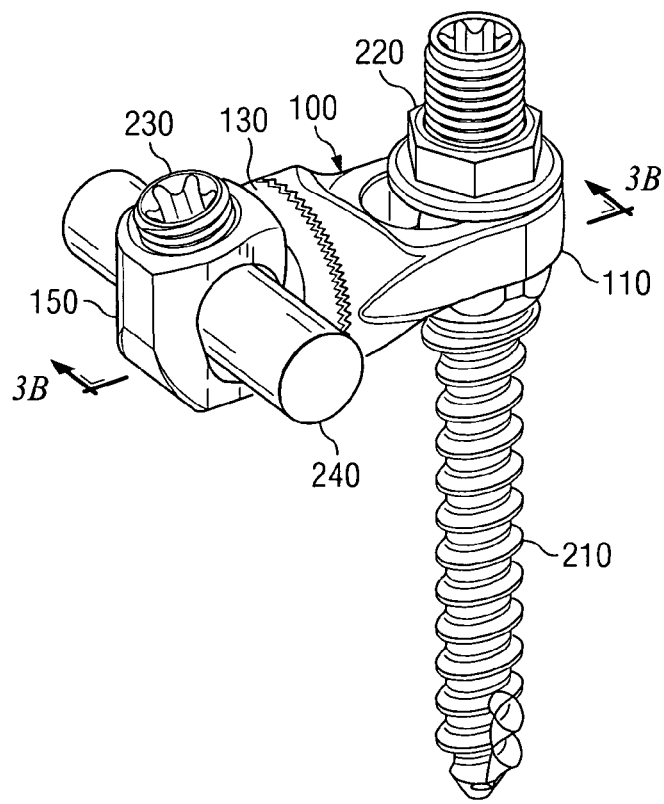
Fig. 3A

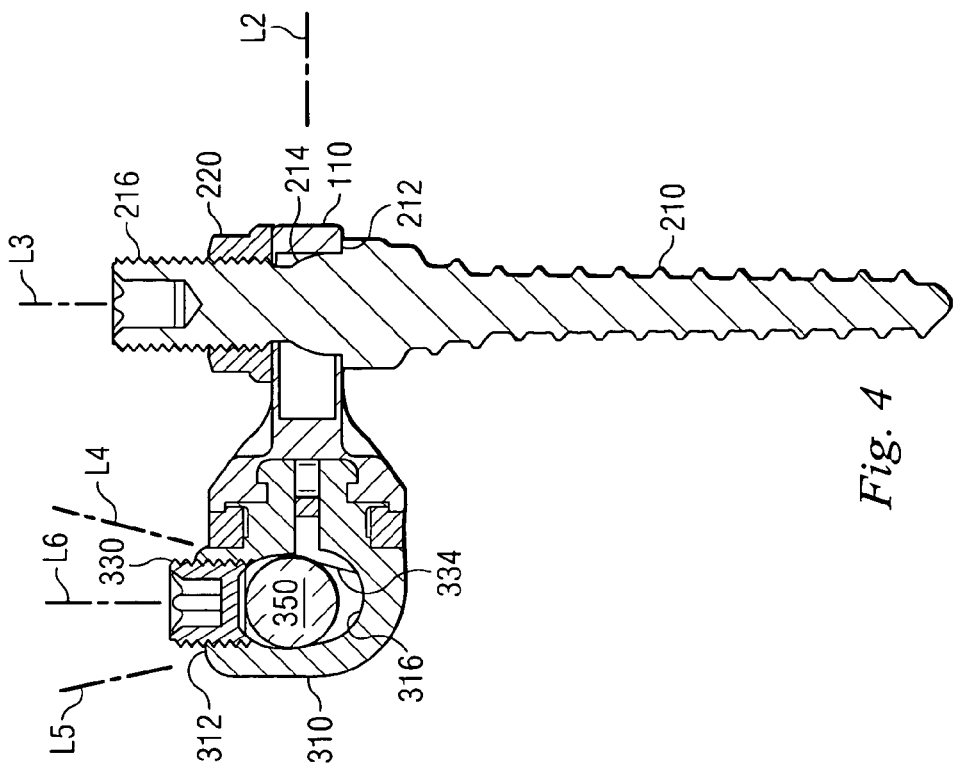
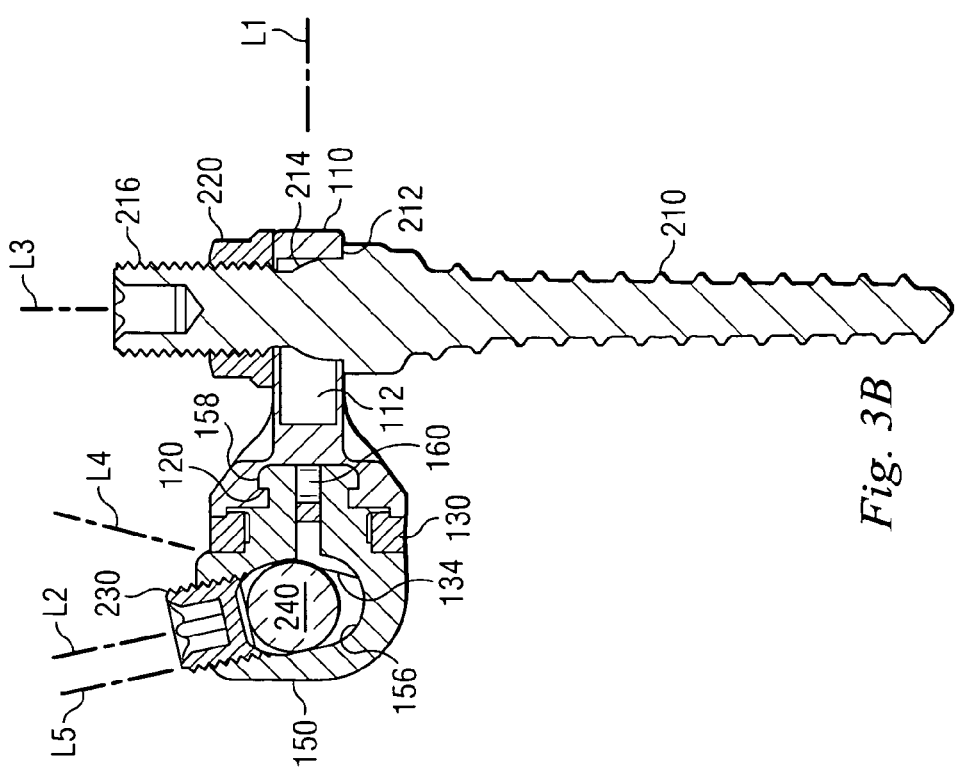

LATERAL CONNECTOR ASSEMBLY

BACKGROUND OF THE INVENTION

The present invention relates generally to spinal fixation systems, such as systems for use in the fixation of the spine for the treatment of various spinal deformities. Specifically, the present invention contemplates a lateral connector assembly for interconnecting an elongated member, such as a rod or tether, with a bone engaging fastener such as a hook, screw or bolt.

The treatment of spinal deformities and injuries has evolved significantly over the last 30 years. Spinal deformities, such as scoliosis and kyphosis, as well as fractures, spondylolisthesis, and other medical indications have been treated using a system of relatively rigid elongated members spanning the vertebral column. In one type of system, the elongated members constitute a plate that has a number of openings or slots through which bone bolts or bone screws extend. The bone engaging fasteners are threaded into different aspects of the vertebra and fixed to the plate to achieve fixation of the elongated plate. In other procedures, elongated rigid rods are joined to screws or hooks embedded in the spine to fix the relative position of each vertebra. In yet further procedures for dynamic stabilization, an at least partially flexible elongate member is joined to bone engaging fasteners embedded in the spine.

In the implantation of any spinal instrumentation, one goal of the surgeon is to minimize the intrusion into the patient, whether by the amount of implants that must be used, the size of the surgical access opening or by the length of time required to fix the implants within the patient. Further, the system must be easy to use and provide the surgeon with confidence that it will provide the desired stabilization after implantation.

While connectors have been provided that offer various degrees of freedom of movement between the elongated member and the bone fastener, there remains a need for providing an improved connection between the bone fastener and the elongated member.

SUMMARY OF THE INVENTION

The present invention provides a connector assembly for connecting a bone engaging fastener to an elongated member. In one aspect the invention includes a connector for joining the bone engaging fastener to a clamp having a channel for holding the elongated member. A compression member is provided to hold the elongated member in the channel and a mechanism is included in the channel to translate the compression force on the elongated member into a locking force to lock the connector to the clamp. In one embodiment, a locking member is provided with an oblique bearing surface that engage the elongated member. In another embodiment, the channel includes an oblique bearing surface that forces the elongated member against a portion of a locking member that locks the connector to the clamp.

In another aspect, the present invention provides a lateral connector assembly for connecting a bone engaging fastener to an elongated member. In one embodiment, the connector assembly includes a lateral connector having a plate portion and a first connection portion, the plate portion defines an opening configured to receive the bone engaging fastener therethrough and the first connection portion defines a first locking surface. The assembly further includes a clamp having a body defining a channel therethrough sized to receive the elongated member therein and a second connection portion defining a connection axis and configured for engagement with the first connection portion of the lateral connector. A variable angle locking member is disposed between the first connection portion and the second connection portion, the variable angle locking member has a second locking surface for engaging the first locking surface of the lateral connector at a plurality of angular orientations, and the variable angle locking member includes a locking member bearing surface opposite the second locking surface. The locking member bearing surface is disposed at least in part within the channel for engaging the elongated member and disposed at an oblique angle with respect to the connection axis. The system further includes a compression member extending between the clamp and the elongated member, the compression member acting to urge the elongated member against the bearing surface.

Further aspects, forms, embodiments, objects, features, benefits, and advantages of the present invention shall become apparent from the detailed drawings and descriptions provided herein.

BRIEF DESCRIPTION OF THE DRAWINGS

FIG. 2 is a partially exploded perspective of the connector assembly of FIG. 1 in combination with an elongated member and a bone engagement member.

FIG. 3A is a perspective view of the connector of FIG. 2 in an assembled form.

FIG. 3B is a partial cross-sectional view of the connector of FIG. 3A taken along line 3B-3B.

FIG. 4 is a partial cross-sectional view of an alternative embodiment of a connector assembly according to another aspect of the present invention.

DESCRIPTION OF THE PREFERRED EMBODIMENTS

Figure 1:
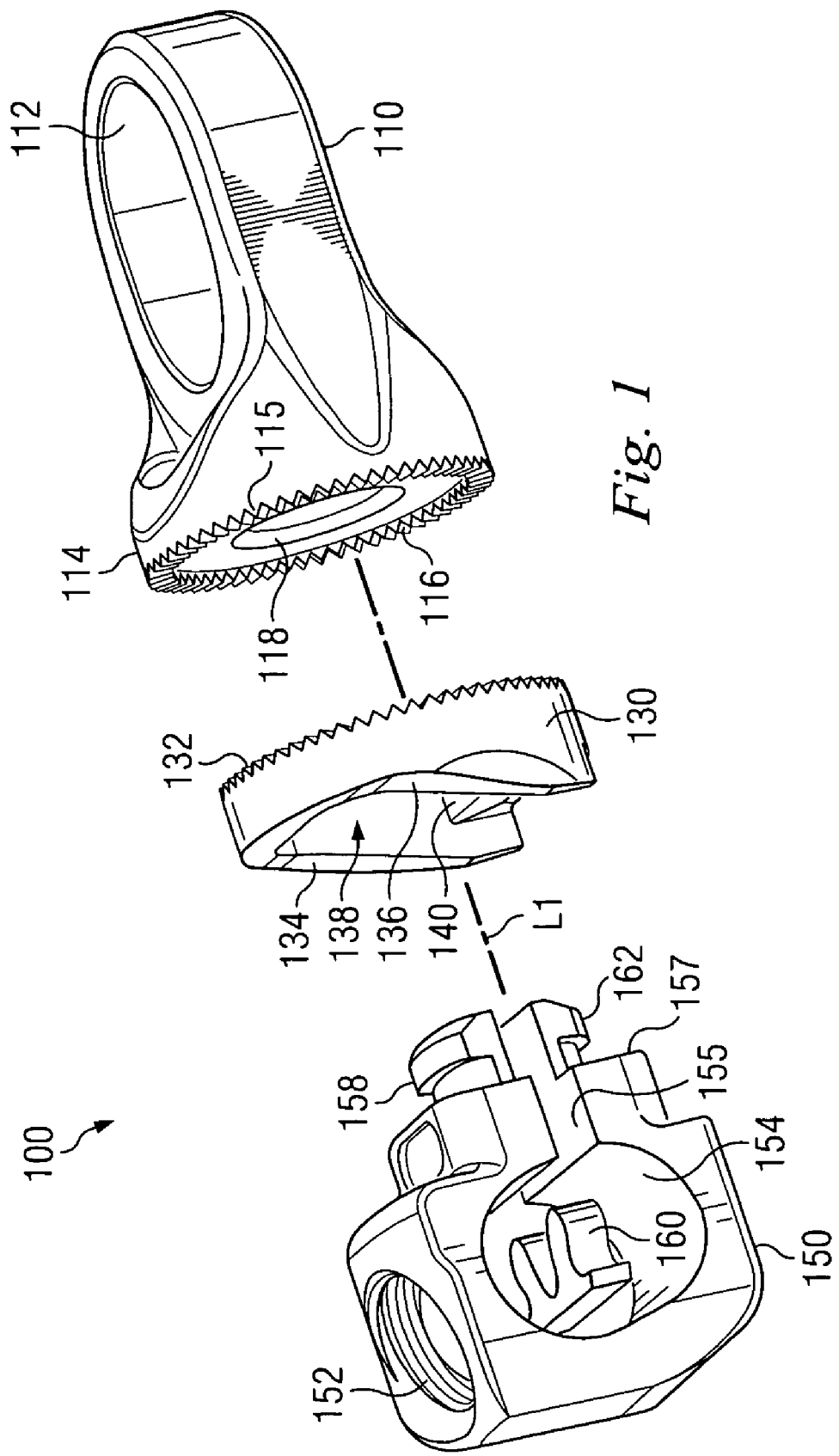
FIG. 1 is an exploded perspective view of a connector assembly according to one aspect of the present invention.

For the purposes of promoting an understanding of the principles of the present invention, reference will now be made to the embodiments illustrated in the drawings, and specific language will be used to describe the same. It will nevertheless be understood that no limitation of the scope of the invention is intended. Any alterations and further modifications in the described devices, instruments, methods, and any further application of the principles of the invention as described herein are contemplated as would normally occur to one skilled in the art to which the invention relates.

Referring now to FIG. 1, there is shown a connector assembly 100 according to the present invention. Connector assembly 100 includes a plate portion 110, a clamp body 150, a variable angle locking washer 130 and a retaining clip 160. The plate portion includes an elongated opening 112 and a connection flange 114 with a locking face 116 having a series of radially emanating splines 115 surrounding connection opening 118. As shown in FIG. 3B, internal connection opening 118 includes an annular groove defining an internal shoulder 120. The variable angle locking washer 130 includes a locking face 132 having a series of radially emanating splines surrounding opening 138 and configured for interdigitating engagement with splines 115 of locking face 116. Locking washer 130 further includes a pair of tapering rod bearing surfaces 134 and 136 spaced on either side of opening 138. Extending between bearing surfaces 134 and 136, is recessed shoulder 140.

Clamp body 150 includes a threaded opening 152 extending into a through channel 154. Extending away from through channel 154 at a substantial perpendicular angle is the connection extension 157. In the illustrated embodiment, the connection extension extends along a connection axis L1 and is divided by gap 155 into upper and lower branches. An upper projection 158 is formed on the upper branch and a lower projection 162 is formed on the lower branch. A retaining clip 160 is adapted to slide along gap 155 and engage internal shoulder 120 of the plate portion 110.

Referring now to FIGS. 2, 3A, and 3B, the connector assembly 100 is shown is an assembled form. Its assembly with be further described below. In FIG. 2, locking washer 130 has been placed about connection extension 157 of the clamp body 150. The connection extension 157 extends through opening 138 in locking washer 130 and has been positioned in connection opening 118. It will be appreciated that gap 155 allows the upper and lower branches of the connection extension 157 to flex inwardly to allow projections 158 and 162 to pass beyond internal shoulder 120. In the illustrated embodiment, the upper and lower branches are formed such that they have a tendency to resiliently return to the position shown in FIG. 3B, with the projections 158 and 162 disposed in the annular groove behind shoulder 120. In this manner, the projections 158 and 162 cooperate with shoulder 120 to retain the connection extension in mated contact with the plate portion 110 as shown in FIG. 3B. With the clamp body 150, locking washer 130 and plate portion 110 in the position shown in FIG. 2, the retaining clip 160 is passed along gap 155 until its legs are seated behind internal shoulder 120 on plate portion 110. In this manner, the retaining clip 160 fills gap 155 to lock the assembly together and thereby prevents the upper and lower branches from flexing inward to release the projections 158 and 162 from the annular groove behind shoulder 120. It will be appreciated that the connection extension 157, lock washer 130 and plate portion 110 are configured such that in the retained position shown in FIG. 2, the plate portion 110 may swivel with respect to the lock washer 130 and clamp body 150. The interconnection between the rectangular shaped shoulder 140 on the lock washer and the rectangular enlarged portion of the connection extension 157 maintains the angular relationship of the lock washer substantially constant with respect to the clamp body 150. In a one aspect, the connector assembly 100 is preassembled into the retained position of FIG. 2 during the manufacturing process and packaged for use.

In the retained positioned the connector assembly 100 is ready for implantation in a patient. In use, a bone fastener, such as bone screw 210 is implanted in the desired position in the patient. Although not illustrated, it is contemplated that bone screw 210 is implanted into the pedicle of a vertebral body along axis L3 for a posterior fixation procedure. Further, a plurality of bone screws 210 are implanted in adjacent spinal levels to complete a posterior fixation procedure. Once the bone screws 210 have been implanted, an elongated spinal rod 240 is selected and cut to a length sufficient to span the plurality of bone screws 210. At least one connector assembly 100 is placed on the rod 240. The connector assembly 100 is in the retained position such that the plate portion 110 may be rotated with respect to the rod clamp body 150. The plate portion 110 is rotated such that the opening 112 is in substantial alignment with the bone screw 210. The upper portion of bone screw 210 is passed through opening 112 in the plate portion 110. An internally threaded nut 220 is connected to the externally threaded post of the bone screw 210 and is advanced to engage the bone screw to the plate portion 110.

The externally threaded set screw 230 is threadedly engaged with the internally threaded side walls of opening 152. Set screw 230 advances along compression axis L2 as shown in FIG. 3B. As set screw 230 advances along compression axis L2, the rod 240 is urged in the direction of compression axis L2. In the embodiment shown in FIG. 3B, bearing wall 156 of the clamp channel 154 extends in a plane aligned with axis L5 that is in substantially parallel alignment with axis L2. As rod 240 moves in the direction L2 along bearing surface 156, the rod 240 engages a portion of locking member bearing surfaces 134 and 136 that extend into channel 154. Locking member bearing surfaces 134 and 136 extend in a locking member bearing plane in substantial alignment with axis L4. In the illustrated embodiment, axis L5 of the clamp bearing surface and axis L4 of the locking member bearing surface intersect to form an acute angle within the channel 154. In this manner, the channel 154 has a first width substantially aligned with connection axis L1 adjacent the set screw and opening 152, and a second width substantially aligned with connection axis L1 and disposed opposite the set screw 230. The first width is greater than the second width. The first width is greater than the diameter of rod 240 while the second width is less than the diameter of rod 240.

In the illustrated embodiment, the sloping wall 156 and corresponding sloping walls 134 and 136 form a channel with side walls that taper from the top, adjacent the set screw, to the bottom of the channel. As the set screw 230 pushes rod 240 into the tapered channel 154, the set screw compression force is translated by the sloping bearing walls 156, and locking member bearing walls 134 and 136 into a locking force applied along axis L1. In the illustrated embodiment the locking member bearing surfaces 134 and 136 are disposed at an oblique angle with respect to the connection axis L1 and the compression axis L2. The clamp bearing surface is also positioned oblique to connection axis L1. This locking force applied against bearing walls 134 and 136 urges the locking member 130 splines into locking engagement with the projecting splines 115 of the connection portion 114 of the plate 110. It will be appreciated that the set screw compression force on rod 240 causes movement of the locking washer 130 along the locking axis L1. Further, movement of the set screw moves rod 240 along bearing surfaces 134 and 136, and clamp bearing surface 156 toward the bottom of the channel. It will be appreciated that rod 240 is positionable in an infinite number of positions along the bearing surfaces. Moreover, with the locking member 130 fully engaged with the connection portion 114, further compression force applied by set screw 230 tends to tighten the locking force applied along axis L1 and to hold rod 230 in a three point contact lock to inhibit movement of the clamp 150 along the rod 240. The tightened set screw holds the connector assembly in a locked position as shown in FIGS. 3A and 3B. The three point contact lock is formed by the engagement between the rod 240 with the set screw 230, the clamp bearing wall 156 and the split locking member bearing wall defined by surfaces 134 and 136. Also, in a plane taken along axis L1, the rod is held in a three point lock position between clamp bearing wall 156 and the locking member bearing walls defined by surfaces 134 and 136 that are spaced wider than the width transverse to axis L1 of the bearing surface 156.

In a further embodiment shown in FIG. 4, the clamp body 310 has an internally threaded bore 312 extending along an axis L6 that is in substantial alignment with axis L3 of the bone fastener and substantially perpendicular to the locking axis L2. Externally threaded set screw 330 is positioned in the bore 312 and exerts a compression force along axis L6. The channel of the clamp body is formed substantially as described above. As rod 350 is advanced along axis L6 into the tapered channel, the rod 350 bears against clamp bearing surface 316 causing the rod to translate along the locking axis L2 as it slides along the bearing surfaces. Continued compression force along axis L6 forces the rod 330 against locking member bearing surface 334 and results in translation of the locking member along the locking axis to lock against the connection portion of the plate. It will be appreciated that in the embodiment illustrated in FIG. 4, the clamp channel is configured to transfer the compressive force of the locking member into a locking force in a substantially perpendicular direction. Further, in the illustrated embodiment, the set screw 330 and axis L6 extend in a direction that substantially bisects the acute angle between oblique clamp bearing surface 316 extending along axis L5 and the oblique locking member bearing surface 334 extending along axis L4.

Although the above illustrated embodiments have been described in detail for the purpose of illustration and understanding of the principles of the present invention, it is contemplated that the invention may be applied in a variety of spinal stabilization assemblies. For example, in one embodiment the clamp body and locking washer combination of the present invention may be applied to the lateral connector of U.S. Pat. No. 5,976,135 to Sherman et al., incorporated herein by reference in its entirety. In another embodiment the connection portion of the plate member is moveable with respect to the portion of the plate member engaging the bone fastener. The moveable connection portion translates along the connection axis in response to the transmission of the set screw compressive force being translated by a clamp body assembly according to the present invention to translate the rod along the locking axis and thereby move the assembly to a locked position. As set forth in U.S. Pat. No. 6,579,292 to Taylor and U.S. Pat. No. 5,885,285 to Simonson, incorporated herein by reference in their entirety, the moveable connection portion slides along the plate member to capture and hold the bone screw without the need for a separate locking nut. Still further, in another embodiment, the plate member may be substantially ring shaped such that it is joined to a shaft of a bone fastening element.

Although a set screw has been shown as the compression member in the illustrated embodiment, in another embodiment, the compression member is an external nut with internal threading that engages an externally threaded portion of the clamp body. In still a further embodiment, the compression member is one or more tapered sleeves that slide along the rod to lock the rod in the channel.

The connector assembly is useful for rigid rods and flexible connectors. For example, in one embodiment, rod 240 is formed of a rigid material such as titanium or stainless steel. In another embodiment, rod 240 is flexible. In such an embodiment, rod 240 is formed of plastic or a flexible metal. In still a further embodiment, the elongate member is not a rod but a flexible cable or cord that may be tensioned between adjacent spinal levels and connectors. Still further, lateral refers to the connection of the elongated member along one side of the shaft of the bone fixation element such as screw 210 as opposed to fixing the elongated member in line with the axis of the bone screw.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A lateral connector assembly for connecting a bone engaging fastener to an elongated member, comprising:

a lateral connector having a plate portion and a first connection portion, said plate portion defining an opening configured to receive the bone engaging fastener therethrough and said first connection portion defining a first locking surface;

a clamp having a body defining a channel therethrough sized to receive the elongated member therein and a second connection portion defining a connection axis and configured for engagement with said first connection portion of said lateral connector, said channel including a proximal portion and a distal portion relative to the connection axis, wherein said distal portion of the channel is closer to the lateral connector than said proximal portion, said proximal portion having a clamp bearing surface disposed along a plane that intersects said connection axis, said second connection portion including a flexible upper extension and a flexible lower extension separated by an extension opening that extends into the channel, the extension opening enabling the upper and lower extensions to flex inwardly toward one another;

a variable angle locking member disposed between said first connection portion and said second connection portion, said variable angle locking member having a second locking surface for engaging said first locking surface of said lateral connector at a plurality of angular orientations, and said variable angle locking member having a locking member bearing surface opposite said second locking surface, said locking member bearing surface disposed at least in part within said channel for engaging the elongated member and disposed at an oblique angle with respect to said connection axis; and a compression member extending between said clamp and said elongated member, said compression member acting to urge said elongated member against said locking member bearing surface and said clamp bearing surface to translate a compressive force exerted by the compression member into a locking force applied along the connection axis.

2. The connector of claim 1, wherein said locking member bearing surface extends substantially along a bearing plane and said second locking surface extends substantially along a locking plane, said bearing plane oriented to intersect said locking plane.

3. The connector of claim 1, wherein said locking member bearing surface has a length and is configured for engaging said elongated member in an infinite number of positions along the length of said locking member bearing surface.

4. The connector of claim 1, wherein said compression member has a compression axis, said compression axis substantially perpendicular to said connection axis.

5. The connector of claim 1, wherein said clamp includes a threaded bore and said compression member is a threaded set screw adapted to be received in said threaded bore.

6. The connector of claim 4, wherein said compression axis intersects said locking member bearing plane such that advancement of said compression member against the elongated member urges the elongated member toward said locking member bearing surface.

7. The connector of claim 1, wherein said clamp bearing surface is disposed at an oblique angle with respect to said connection axis.

8. The connector of claim 7, wherein said elongated member engages said clamp bearing surface, said locking member bearing surface and said compression member in a three point connection in a locked position.

9. The connector of claim 7, wherein said channel of said clamp has a first width adjacent said compression member and a second width between said clamp bearing surface and said locking member bearing surface substantially opposite said compression member, said first width greater than said second width.

10. A lateral connector assembly for connecting a bone engaging fastener to an elongated member, comprising:
 a lateral connector having a plate portion and a first connection portion, said plate portion defining an opening configured to receive the bone engaging fastener therethrough and said first connection portion defining a first locking surface;
 a clamp having a body defining a channel therethrough sized to receive the elongated member therein and a second connection portion defining a connection axis and configured for engagement with said first connection portion of said lateral connector, said channel including a proximal portion and a distal portion relative to the connection axis, wherein said distal portion of the channel is closer to the lateral connector than said proximal portion, said proximal portion of channel including a clamp bearing surface configured for engaging said elongated member substantially opposite said second connection portion, the clamp bearing surface disposed at an oblique plane that intersects said connection axis, the second connection portion including a flexible upper extension and a flexible lower extension separated by an extension opening that extends into the channel, the extension opening enabling the upper and lower extensions to flex inwardly toward one another;
 a variable angle locking member disposed between said first connection portion and said second connection portion, said variable angle locking member having a second locking surface for engaging said first locking surface of said lateral connector at a plurality of angular orientations, and said variable angle locking member having a locking member bearing surface opposite said second locking surface, said locking member bearing surface disposed at least in part within said channel for engaging the elongated member; and
 a compression member extending between said clamp and said elongated member, said compression member acting to urge said elongated member against said clamp bearing surface and said locking member bearing surface to translate a compressive force exerted by the compression member into a locking force applied along the connection axis to lock said first locking surface to said second locking surface.

11. The connector of claim 10, wherein said clamp bearing surface has a length and is configured for engaging said elongate member in an infinite number of positions along the length of said clamp bearing surface.

12. The connector of claim 10, wherein said locking member bearing surface is disposed at a second oblique angle with respect to said connection axis.

13. The connector of claim 12, wherein said elongated member engages said clamp bearing surface, said locking member bearing surface and said compression member in a three point connection in a locked position.

14. The connector of claim 12, wherein said channel of said clamp has a first width adjacent said compression member and a second width between said clamp bearing surface and said locking member bearing surface substantially opposite said compression member, said first width greater than said second width.

15. The connector of claim 10, wherein said clamp bearing surface and said locking member bearing surface define an acute angle therebetween.

16. The connector of claim 15, wherein the compression member acting to urge said elongated member defines a compression axis that substantially bisects said acute angle.

17. The connector of claim 15, wherein the compression member acting to urge said elongated member defines a compression axis that is substantially aligned with said clamp bearing surface.

18. A connector assembly for connecting a bone engaging fastener to an elongated member, comprising:
 a connector having a bone engagement portion for fixation to a bone and a first connection portion defining a first locking surface;
 a clamp having a body defining a channel therethrough sized to receive the elongated member therein and a second connection portion defining a connection axis and configured for engagement with said first connection portion of said connector, said channel including a proximal portion and a distal portion relative to the connection axis, wherein said distal portion of the channel is closer to the connector than said proximal portion, the second connection portion including a flexible upper extension and a flexible lower extension separated by an extension opening that extends into the channel, the extension opening enabling the upper and lower extensions to flex inwardly toward one another;
 a variable angle locking member disposed between said first connection portion and said second connection portion, said variable angle locking member having a second locking surface for engaging said first locking surface of said lateral connector at a plurality of angular orientations, and said variable angle locking member having a locking member bearing surface opposite said second locking surface;
 a compression member extending between said clamp and said elongated member along a compression axis, said compression member applying a compression force along said compression axis on said elongated member; and
 means disposed in the proximal portion of said channel and along a plane that intersects said connection axis, said means for translating said compression force along said compression axis on said elongated member into a locking force directed along said connection axis to urge said elongated member against said locking member bearing surface to thereby lock said first locking surface to said second locking surface.

19. The connector of claim 18, wherein said means for translating includes at least one bearing surface disposed at an oblique angle with respect to said connection axis.

20. The connector of claim 1, further comprising a retaining clip adapted to slide along the connection axis into the extension opening to inhibit inward flexion of the upper and lower extensions relative to each other.

* * * * *